US00PP17199P2

(12) United States Plant Patent
Jonkers

(10) Patent No.: US PP17,199 P2
(45) Date of Patent: Nov. 7, 2006

(54) ***DIASCIA* PLANT NAMED 'DALA PINKA'**

(50) Latin Name: *Diascia barberae*
Varietal Denomination: Dala Pinka

(75) Inventor: Johanna B. Jonkers, Andijk (NL)

(73) Assignee: Goldsmith Seeds, Inc, Gilroy, CA (US)

( * ) Notice: Subject to any disclaimer, the term of this patent is extended or adjusted under 35 U.S.C. 154(b) by 0 days.

(21) Appl. No.: 11/269,352

(22) Filed: Nov. 8, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

| | | | | | |
|---|---|---|---|---|---|
| PP13,949 | P2 | * | 7/2003 | Stemkens | Plt./263 |
| PP14,782 | P2 | * | 5/2004 | Stemkens | Plt./263 |
| PP16,044 | P2 | * | 10/2005 | Schrader | Plt./263 |
| 2006/0117433 | P1 | * | 6/2006 | Stemkens | Plt./263 |

OTHER PUBLICATIONS

UPOV ROM GTITM Computer Database, GTI Jouve Retrieval Software 2005/05 Citations for 'Dala Pinka'.*

* cited by examiner

*Primary Examiner*—Wendy Haas
(74) *Attorney, Agent, or Firm*—Jondle & Associates P.C.

(57) ABSTRACT

A new *Diascia* plant particularly distinguished by pink flowers with reddish markings on the inner part of the flower, medium-green foliage with medium to large rounded leaves, medium to vigorous growth habit with semi-upright branches, uniform and round plant habit, and early to flowering is disclosed.

1 Drawing Sheet

Genus and species: *Diascia barberae.*
Variety denomination: 'Dala Pinka'.

BACKGROUND OF THE NEW PLANT

The present invention comprises a new and distinct cultivar of *Diascia,* botanically known as *Diascia barberae,* and hereinafter referred to by the cultivar name 'Dala Pinka'. The new cultivar originated from a hybridization made in 2002 in Andijk, The Netherlands. The female parent is a proprietary *Diascia* plant designated 'DSY-16-1' (unpatented), having lilac-rose flower color and the male parent is a proprietary *Diascia* plant designated 'DSY-2-1' (unpatented), having a salmon flower color. The seeds produced by the hybridization were sown in November 2002, and the resulting seedlings were selected in February 2003. A single plant selection was chosen for further evaluation and for asexual propagation in the summer of 2003.

The new cultivar was created in 2002 in Andijk, The Netherlands and has been asexually reproduced repeatedly by vegetative cuttings and tissue culture micropropagation in Andijk, The Netherlands over a two-year period. The plant has also been trialed at Gilroy, Calif., and Andijk, The Netherlands. The present invention has been found to retain its distinctive characteristics through successive asexual propagations.

Plant Breeder's Rights for this cultivar were applied for in Europe on Jan. 24, 2005 and in Canada on Jul. 19, 2005.

SUMMARY OF THE INVENTION

The following are the most outstanding and distinguishing characteristics of this new cultivar when grown under normal horticultural practices in Gilroy, Calif. and Andijk, The Netherlands.

1. Pink flowers with reddish markings on the inner part of the flower;
2. Medium green foliage with medium to large rounded leaves;

3. A medium to vigorous growth habit with semi-upright branches;
4. A uniform and round plant habit; and
5. Early flowering.

DESCRIPTION OF PHOTOGRAPH

This new *Diascia* plant is illustrated by the accompanying photograph which shows blooms, buds, and foliage of the plant in full color; the colors shown are as true as can be reasonably obtained by conventional photographic procedures. The photograph is of three 6-month-old plants grown in a greenhouse with natural light in a spring trial setting.

The accompanying photograph shows blooms, buds, mature foliage, and plant habit; the inset shows mature inflorescences and buds.

DESCRIPTION OF THE NEW CULTIVAR

The following detailed descriptions set forth the distinctive characteristics of 'Dala Pinka'. The data which define these characteristics were collected from asexual reproductions carried out in Hillscheid, Germany. The plant history was taken on seven-month-old plants grown, 3 plants each, in 35-cm-diameter baskets (capable of holding 5-liters of soil) in an outdoor trial field under poly-cover rain protection. Color readings were taken under natural light. Color references are primarily to The R.H.S. Colour Chart of The Royal Horticultural Society of London (R.H.S.) (2001 edition). Texture description details were observed under a magnifying glass.

DESCRIPTION OF THE NEW PLANT

Classification:
*Family.*—Scrophulariaceae.
*Botanical name.*—*Diascia barberae* Hook.

Parentage:

*Female parent.*—'DSY-16-1' a proprietary lilac-rose-colored *Diascia* plant (unpatented).

*Male parent.*—'DSY-2-1' a proprietary salmon-colored *Diascia* plant (unpatented).

Growth:

*Form and growth habit.*—Round plant with both upright and semi-trailing branches; appears bushy and well branched; medium to strong vigor.

*Height.*—22 cm (from top of soil) for 7-month-old plants to 36 cm (total vertical height) of a plant in a hanging basket.

*Width.*—72 cm for a 7-month-old plant.

*Spread* (*including flowers*).—60–65 cm, from the base of the main stem to the tips of the branches.

*Time to produce a finished flowering plant.*—About 10 weeks for a 5-inch pot.

*Outdoor plant performance.*—Plant in full sun; is free-flowering through the summer; has some heat tolerance; use in mixed container planting or mass planting in a bed.

*Time to initiate and develop roots.*—About 20 days in the spring.

*Root description.*—Fibrous and freely branching.

Leaves:

*Arrangement.*—Single and decussate.

*Shape.*—Cordate.

*Apex.*—Obtuse.

*Base.*—Weakly cordate.

*Margin.*—Weakly serrate.

*Immature.*—Color: Upper surface: Between RHS 137D and RHS 143A. Lower surface: RHS 138B. Texture: Finely pubescent.

*Mature* (*fully expanded*).—Length: 2.2–2.5 cm. Width: 2.1–2.2 cm. Color: Upper surface: RHS 137B to RHS 137C. Lower surface: RHS 138B.

*Venation.*—Type: Pinnate. Color: RHS 144B.

*Texture.*—Smooth, glabrous.

*Petiole.*—Length: 0.2–0.3 cm. Width: 0.2 cm. Color: RHS 144A.

Stems:

*Length.*—40 to 45 cm without the inflorescence.

*Diameter.*—0.3–0.4 cm as measured in the middle (is square not round).

*Internode length.*—1.5–3.0 cm.

*Color.*—RHS 143B.

*Texture.*—Appears smooth and glabrous, but has sparse pubescence.

*Anthocyanin.*—Absent.

Flower bud:

*Shape.*—Round base and conical (flattened).

*Diameter.*—0.7 cm.

*Length.*—0.4 cm.

*Color* (*at tight bud*).—RHS 75B and RHS N77B at the base.

Inflorescence:

*Inflorescence type.*—Terminal raceme with flowers in an alternate arrangement.

*Blooming habit.*—Continuously.

*Quantity of inflorescences per plant.*—100.

*Lastingness of individual blooms on the plant.*—3–4 days, depending on weather conditions.

*Fragrance.*—None.

*Inflorescence length.*—10 cm.

*Peduncle.*—Color: RHS 143A. Length: 9.5 cm. Diameter: 0.2 cm. Texture: Finely pubescent.

Flower:

*Type.*—Single, zygomorphic; 5-lobes fused at the base.

*Quantity* (*per raceme*).—Solitary at a distance of 0.5 to 1.0 cm; usually 3–5 open flowers at the same time; about 20 flowers and buds in various stages of development.

*Shape.*—Salver-shaped.

*Length.*—2.1–2.2 cm.

*Depth.*—0.5 cm.

*Width.*—2.0–2.1 cm.

*Color.*—General: Mainly bluish-pink with contrasting reddish-purple inner coloring. Upper surface: RHS 68B. Lower surface: RHS 75C. Corolla (inside color): RHS 67A; upper petals have a patch of RHS 12A (yellow) at the base.

*Petals* (*lobes*).—Quantity: 5. Arrangement: Two upper lobes (mainly fused) with two lateral lobes and one lower lobe. Apex: Rounded. Base: Fused. Margin: Entire. Texture: Smooth and papillose.

*Upper lobes, size.*—Length (from the Corolla opening): 0.4–0.5 cm. Width: 1.0 cm.

*Lateral lobes, size.*—Length (from the Corolla opening): 0.5 cm. Width: 0.7 cm. Spur: Shape: Funnel-shaped and directed downwards. Length: 0.8 cm. Diameter: 0.3 cm. Color: RHS 67C to RHS 79D at the tip.

*Lower lobe.*—Length (from the Corolla opening): 1.0–1.1 cm. Width: 1.4–1.5 cm.

*Sepals.*—Quantity: 5. Color: RHS 143A. Length: 0.2 cm. Width: 0.1 cm. Shape: Lanceolate. Apex: Acute. Base: Fused. Anthocyanin: Absent. Texture: Rough, pubescent.

*Pedicels.*—Color: RHS 143C (light-green). Length: 1.3–1.8 cm. Diameter: 0.1 cm. Texture: Finely pubescent.

Reproductive organs:

*Stamens.*—Quantity: 4; coherent, arching towards and somewhat twisting around the pistil. Filament: Color: RHS 79D (purple). Length: 0.3 cm. Diameter: 0.1 cm. Anther color: RHS 14D (pale yellow). Pollen amount: Abundant. Pollen color: RHS 12A.

*Pistils.*—Quantity: 1. Length: 0.3 cm. Stigma color: RHS 143D (light-green). Style color: RHS 145B.

Fruit and seed set: Has not been observed.

Disease and insect resistance: Has not been observed.

COMPARISON WITH PARENTAL AND COMMERCIAL CULTIVARS

'Dala Pinka' differs from the female parent, proprietary *Diascia* plant 'DSY-16-1' (unpatented), in that 'Dala Pinka' has a less bluish flower color, is earlier to flower, and has a more upright plant habit than 'DSY-16-1'.

'Dala Pinka' differs from the male parent, proprietary *Diascia* plant 'DSY-2-1' (unpatented), in that 'Dala Pinka' has pink flowers while 'DSY-2-1' has salmon colored flowers. Additionally, 'Dala Pinka' has a more freely branching plant habit than 'DSY-2-1'.

'Dala Pinka' differs from the commercial cultivar 'Diastara' (U.S. Plant Pat. No. 14,782) in that 'Dala Pinka' has larger, deeper pink flowers and is earlier to flower than 'Diastara'.

'Dala Pinka' differs from the commercial cultivar 'Diastu' (U.S. Plant Pat. No. 13,949) in that 'Dala Pinka' has more distinct reddish markings on the inner part of the corolla than 'Diastu'. Additionally, 'Dala Pinka' has stronger partly-upright stems, while 'Diastu' has prostrate to spreading stems with finer and stronger branched shoots.

I claim:

1. A new and distinct cultivar of *Diascia* plant as shown and described herein.

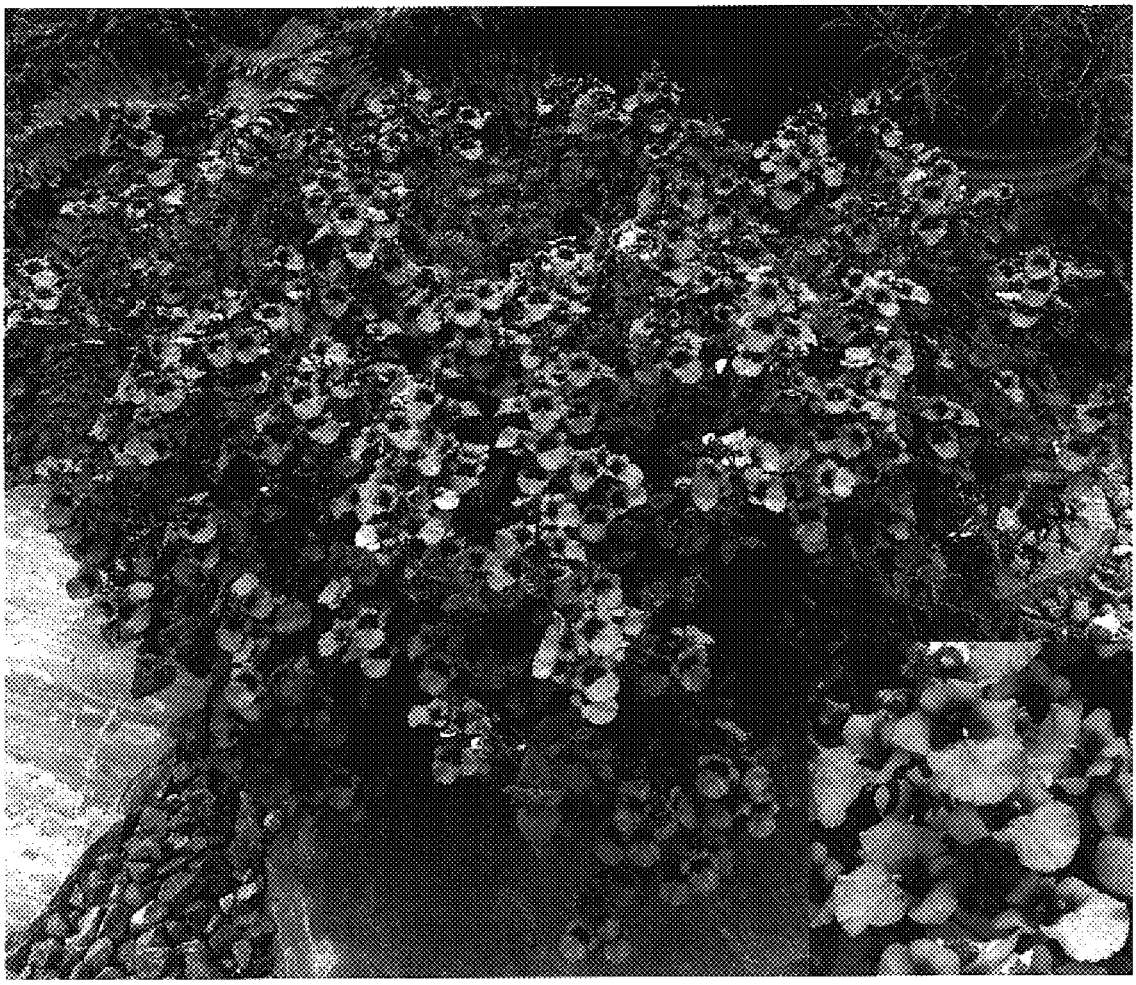

* * * * *